(12) United States Patent
Ernster

(10) Patent No.: US 8,898,846 B2
(45) Date of Patent: Dec. 2, 2014

(54) CLEANER FOR SUCTION COAGULATOR

(76) Inventor: Joel A. Ernster, Colorado Springs, CO (US)

( * ) Notice: Subject to any disclaimer, the term of this patent is extended or adjusted under 35 U.S.C. 154(b) by 939 days.

(21) Appl. No.: 13/043,241

(22) Filed: Mar. 8, 2011

(65) Prior Publication Data

US 2011/0154591 A1   Jun. 30, 2011

Related U.S. Application Data

(63) Continuation-in-part of application No. 11/534,641, filed on Sep. 23, 2006, now abandoned.

(60) Provisional application No. 60/720,269, filed on Sep. 23, 2005.

(51) Int. Cl.
*B08B 9/023* (2006.01)
*B08B 1/00* (2006.01)
*A61B 19/00* (2006.01)
*B08B 9/00* (2006.01)

(52) U.S. Cl.
CPC . *B08B 1/00* (2013.01); *A61B 19/34* (2013.01); *B08B 9/00* (2013.01)
USPC ............................................ 15/104.04; 15/88

(58) Field of Classification Search
USPC .................... 15/104.03, 104.04, 88
See application file for complete search history.

(56) References Cited

U.S. PATENT DOCUMENTS

| 3,266,075 | A | * | 8/1966 | Conrad | 15/104.03 |
|---|---|---|---|---|---|
| 4,014,063 | A | | 3/1977 | Bunke | |
| 4,637,392 | A | | 1/1987 | Sorochenko | |
| 5,566,416 | A | | 10/1996 | Karls | |
| 5,908,253 | A | | 6/1999 | Sutter | |
| 6,250,315 | B1 | | 6/2001 | Ernster | |
| 6,813,797 | B1 | | 11/2004 | Kadinger | |

* cited by examiner

*Primary Examiner* — Randall Chin

(57) ABSTRACT

A cleaning device for cleaning a coagulator has a housing defining an interior chamber with a prong extending along a central axis to receive a coagulator bore. An insertion guide with an opening along the central axis guides insertion of the tip of the coagulator onto the prong. Pliable wipers extend inward from the sidewalls of the chamber toward the prong, so that the wipers deform by contact to wipe against the coagulator in operation. The wipers can be formed as part of a pliable tubular member that is inserted into the chamber in the housing and held in place by an end cap that incorporates the insertion guide.

12 Claims, 5 Drawing Sheets

CLEANER FOR SUCTION COAGULATOR

RELATED APPLICATIONS

The present application is a continuation-in-part of the Applicant's U.S. patent application Ser. No. 11/534,641, entitled a "Cleaner For Suction Coagulator," filed on Sep. 23, 2006, now abandoned, which is based on and claims priority to the Applicant's U.S. Provisional Patent Application 60/720,269, filed on Sep. 23, 2005. Both of these applications are hereby incorporated by reference in their entireties.

FIELD OF THE INVENTION

The present invention relates to the field of medical instruments. More particularly, the invention relates to a cleaner for cleaning a suction coagulator or like instrument.

DESCRIPTION OF RELATED ART

The present invention is in some ways similar to the device described in the inventor's previously issued U.S. Pat. No. 6,250,315, the contents of which are incorporated herein.

SUMMARY OF THE INVENTION

A cleaning device for cleaning a tubular device such as a coagulator has a housing defining an interior chamber with a prong extending along a central axis to receive a coagulator bore. An insertion guide with an opening along the central axis guides insertion of the tip of the coagulator onto the prong. Pliable wipers extend inward from the sidewalls of the chamber toward the prong, so that the wipers deform by contact to wipe against the coagulator in operation. The wipers can be formed as part of a pliable tubular member that is inserted into the chamber in the housing and held in place by an end cap that incorporates the insertion guide.

BRIEF DESCRIPTION OF THE DRAWINGS

The present invention can be more readily understood in conjunction with the accompanying drawings, in which.

DETAILED DESCRIPTION OF THE INVENTION

Figure 1:
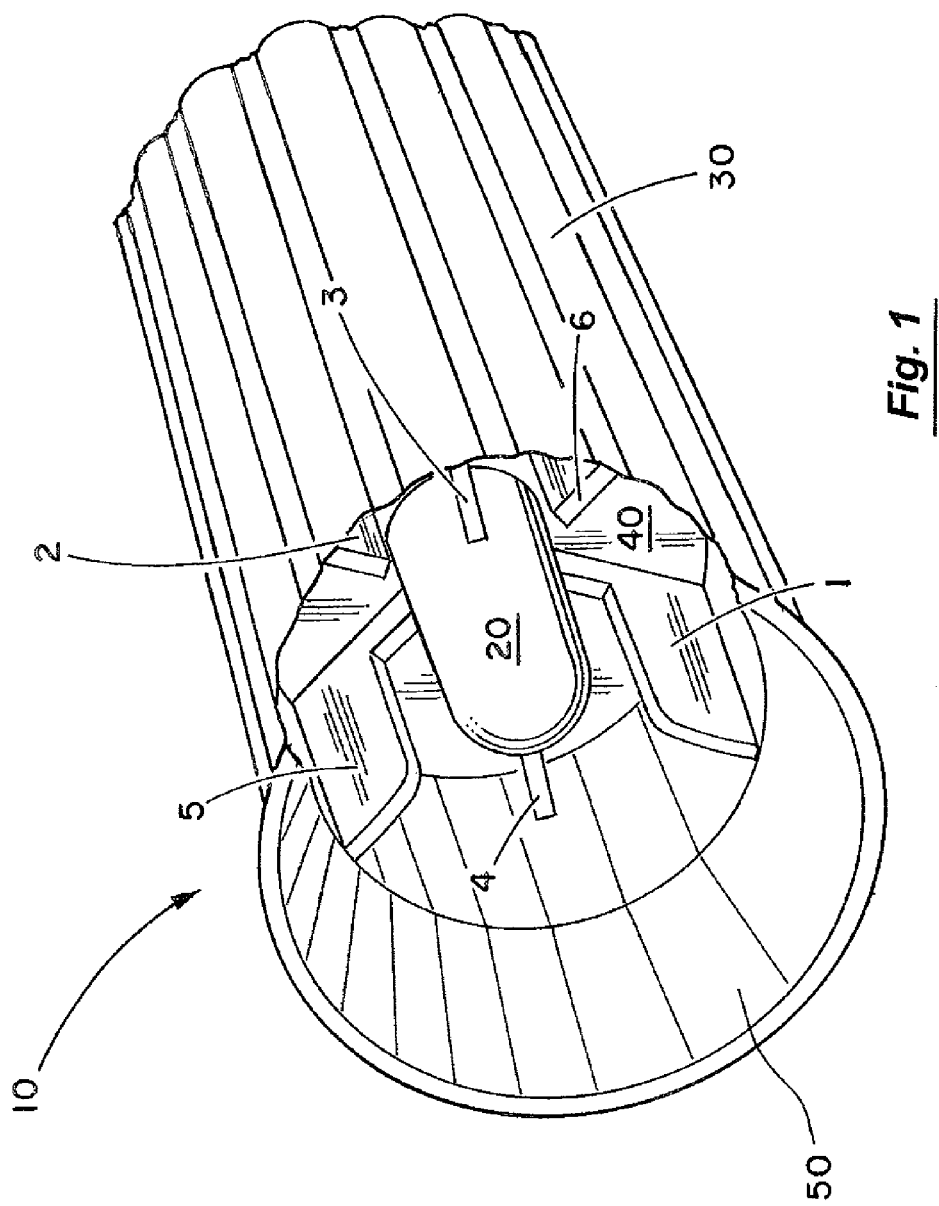
FIG. 1 is a perspective view of a device according to an embodiment of the invention.
Figure 2:
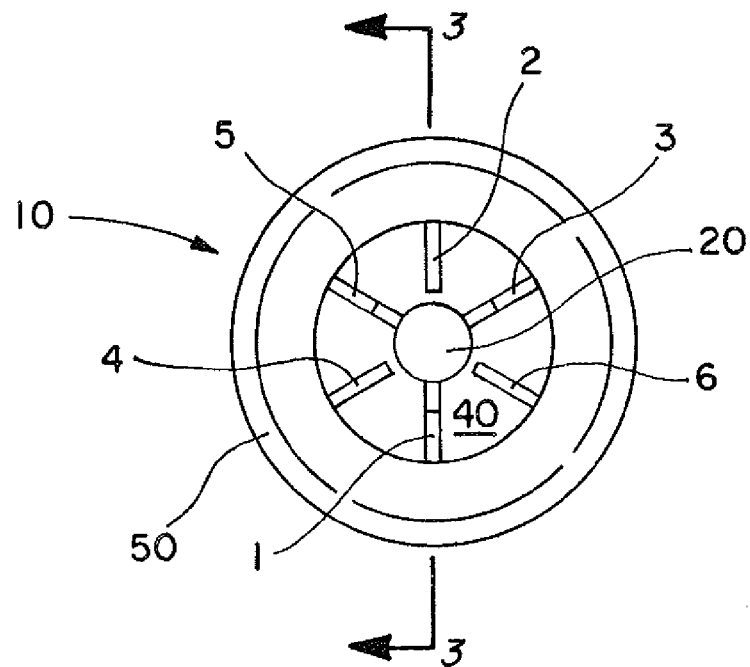
FIG. 2 is a top view of the device.
Figure 3:
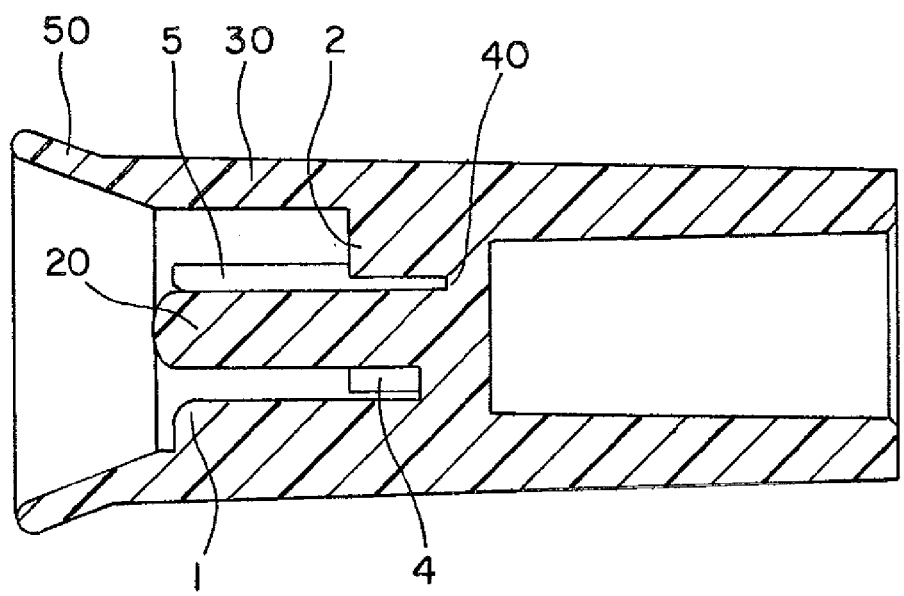
FIG. 3 is a sectional view of the device, taken along the line A-A in FIG. 2.
Figure 4:
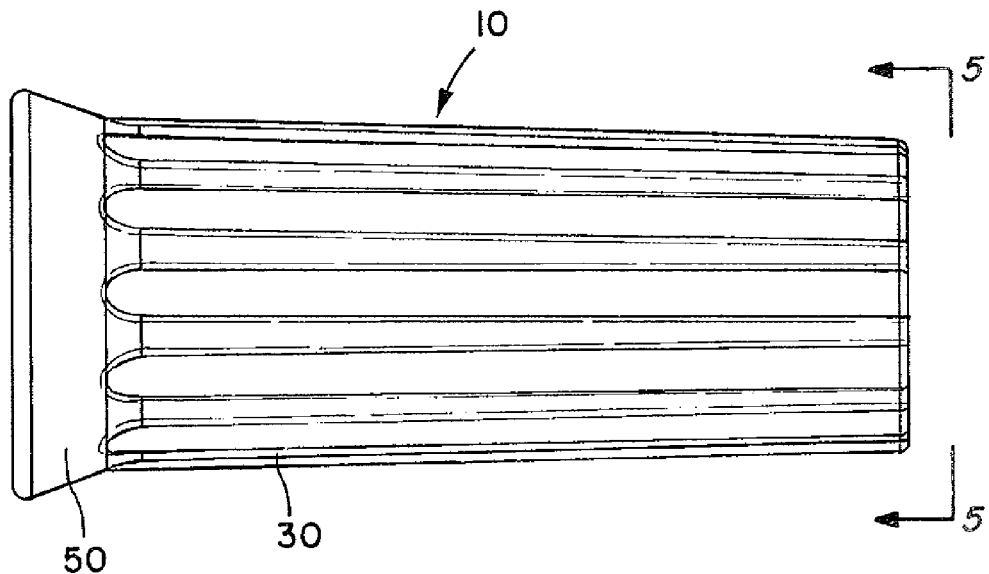
FIG. 4 is a side view of the device.
Figure 5:
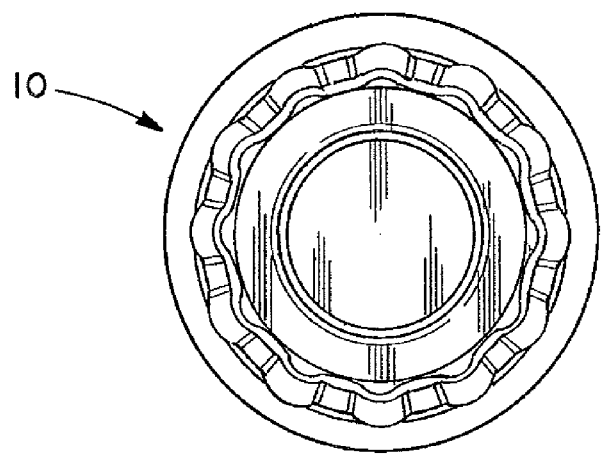
FIG. 5 is a bottom view of the device.

A distinction between the present device and the inventor's previously patented device is the inclusion of six wipers 1-6. It will be appreciated that the number of wipers isn't critical. The purpose of the wipers is that they clean the coagulator tube when the device is used as intended. In use, the user inserts the tube of the coagulator (not shown) into the cleaner 10 so that the tube is axially aligned with the prong 20 situated at least partially within the interior chamber formed by the cylindrical sidewall of the cleaner housing 30. The user then preferably rotates the tube cleaner housing 30 with respect to the coagulator so that the wipers 1-6 wipe the and thereby clean it in connection with the prong 20 and sidewall of the cleaning housing 30.

The wipers are preferably configured as follows. Wipers in a first set of wipers (shown as wipers 1, 3, and 5) extend inward from the sidewall of the cleaner housing 30 to the prong 20 less far than do wipers in a second set of wipers (shown as wipers 2, 4, and 6). Additionally, the first set of wipers (1, 3, 5) extends further from the base 40 toward the aperture of the cleaner than do the second set of wipers (2, 4, 6). That is, from a certain perspective, the wipers in the first set (1, 3, 5) are high and narrow, and the wipers in the second set (2, 4, 6) are low and wide. The third dimension of the wipers, thickness, may be the same or different. A significance of this is that, in operation, the coagulator tube when inserted first contacts the high and narrow wipers (1, 3, 5), and then contacts the low and wide wipers (2, 4, 6) as the coagulator is further inserted.

The disclosed cleaner 10 has certain advantages compared to the device in U.S. Pat. No. 6,250,315. First, the two sizes of wipers are particularly good at cleaning the coagulator because in general it will have a distal exposed tip section (i.e., metal for coagulating) and then a proximal insulated section. The insulated section will have a somewhat greater diameter because of the thickness of the insulation. In operation, the low and wide wipers effectively wipe the relatively narrow tip section, and the high and narrow wipers wipe the insulated section. Moreover, the two sets of wipers are particularly effective in cleaning a range of coagulators as the same cleaning device may be used with coagulators that have somewhat different sizes, either because the coagulators were intended to have different sizes or because of manufacturing tolerances or the accumulation of debris. With two different-sized wipers, one or the other size will likely be adapted to effectively clean the tube (including portions of the tube having different diameters). While the utility of the present device has been explained in the context of a suction coagulator (such as a nasal coagulator), the device may also have applicability in cleaning other tube devices, especially those having a tube of a varying diameter. Optionally, the cleaner 10 may have a flared end portion 50 to help guide insertion of the coagulator tube.

Figure 6:
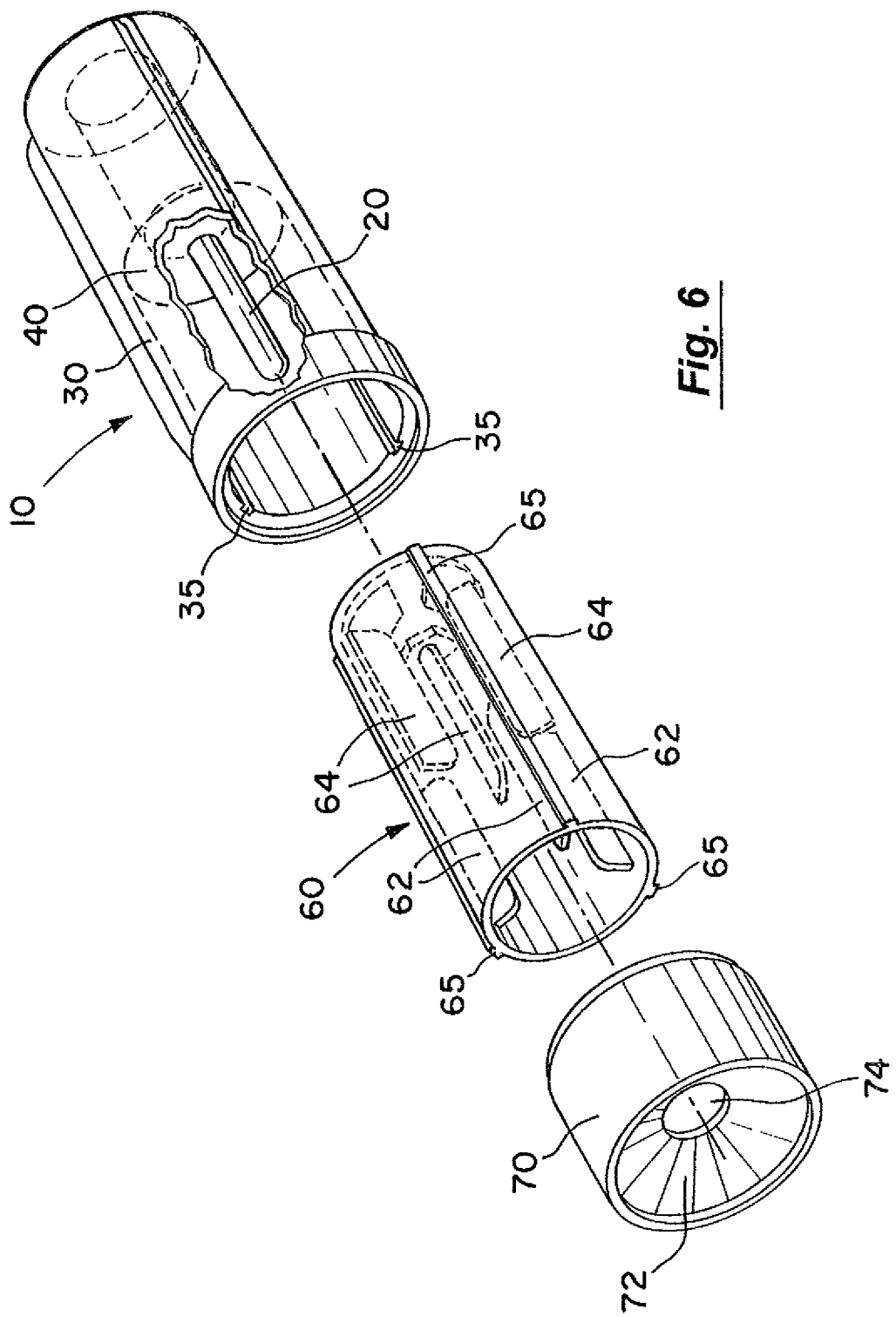
FIG. 6 is an exploded perspective view of an embodiment of the present invention in which the wipers 62, 64 are formed as part of a pliable tubular member 60 that is inserted into the cleaner housing 10.
Figure 7:
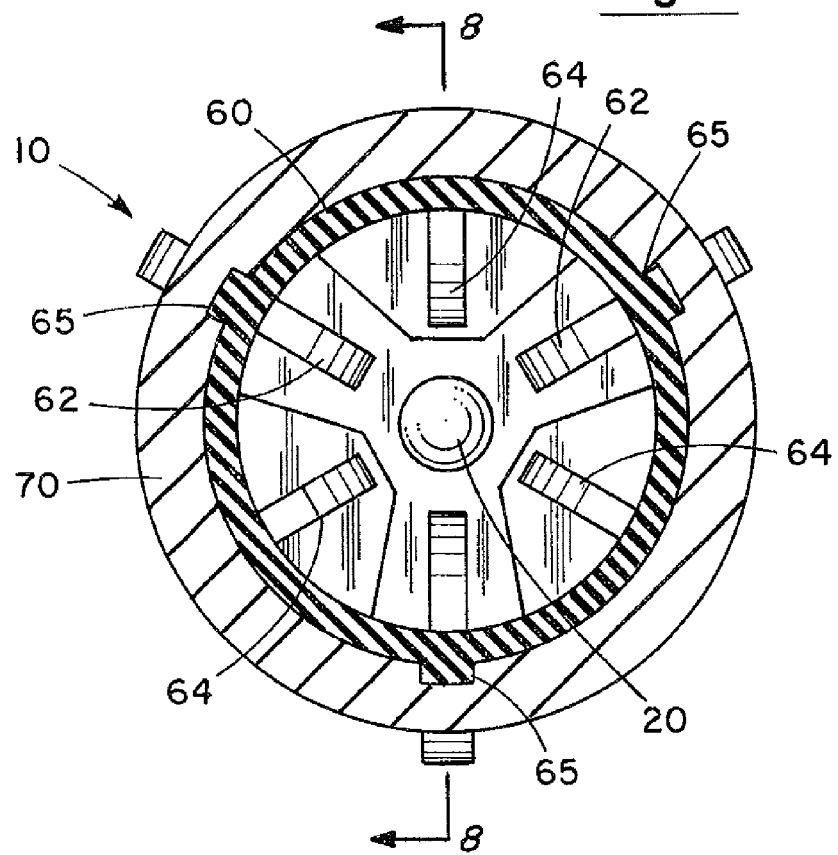
FIG. 7 is a cross-sectional view of assembled device in FIG. 6 taken perpendicular to the central axis of the device.
Figure 8:
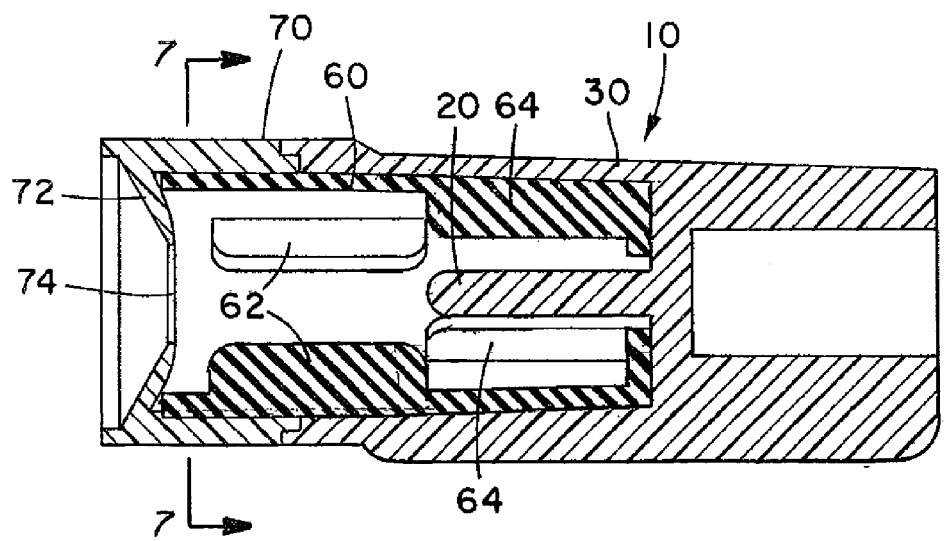
FIG. 8 is a cross-sectional view of the assembled device in FIG. 6 taken along the central axis of the device.

FIG. 6 is an exploded perspective view showing another embodiment of the present invention. FIGS. 7 and 8 are orthogonal cross-sectional views of assembled device. In this embodiment, the wipers 62, 64 are formed as part of a pliable tubular member 60 that is inserted into the cleaner housing 30. In addition, an end cap 70 with a conically-tapered guide 72 helps to properly align the tip of a coagulator with the prong 20 as the coagulator is inserted into the device. The end cap 70 is bonded to the open end of the cleaner housing 30 after the tubular member 60 has been inserted to hold the assembly together, as illustrated in FIG. 8.

The interior of the device housing 30 defines a substantially cylindrical chamber for receiving the pliable tubular member 60. The base 40 supporting the prong 20 forms one end wall of the interior chamber, while the sidewall of the chamber is formed by the interior surface of the housing 30. The opposing end of the chamber is open. As before, a prong 20 extends from the center of the base 40 into the interior chamber. Alternatively, the solid base 40 can be replaced by a web or supports members extending from the device housing 30 to support the prong 20. The interior chamber can be viewed as having a central axis running through the prong 20 toward the open end of the interior chamber.

The tubular member 60 is generally cylindrical and can be made of any suitable pliable or resilient material, such as a soft polymer, rubber, or a foamed polymer. The tubular member 60 has a central passageway running along its central axis with cross-sectional dimensions suitable to accept insertion of the tip of a conventional coagulator. The external diameter of the tubular member 60 is selected so that it will slide snugly into the internal chamber of the device housing 30, and be held in place by contact with the sidewalls of the chamber for support. The exterior surface of the tubular member 60 can be equipped with a series of alignment ribs 65, as shown in FIGS. 6 and 7, that engage complementary slots 35 in the interior wall of the device housing 30 to prevent rotation of the tubular member 60 with respect to the housing 30 when the device is being used. Alternatively, the locations of the alignment ribs 65 and slots 35 can be reversed.

After the tubular member 60 has been inserted into the cleaner housing 10, the central passageway through the tubular member 60 is coaxial with the prong 20 (i.e., aligned with the central axis of the chamber of the device), so that the tubular member 60 tends to guide the tip of the coagulator onto the prong 20 as the coagulator is inserted into the cleaner. Although the tubular member 60 can be made of a soft, pliable material, the surrounding cleaner housing 10 provides rigidity and structural support to the tubular member 60 when the device is in use.

A number of pliable wipers 62, 64 extend into the central passageway of the tubular member 60 toward its central axis. The wipers 62, 64 intrude sufficiently far into the central passageway of the tubular member 60 so that they contact the surface of a coagulator and are deformed to wipe against the side of the coagulator as it is initially inserted into the cleaner and then rotated by the user. Preferably, the wipers 62, 64 extend radially inward, although other configurations could be substituted. The number, arrangement, dimensions, cross-sectional shape and placement of the wipers 62, 64 within the tubular member 60 are largely matters of design choice. For example, multiple sets of wipers 62, 64 can be spaced axially along the tubular member 60, as shown in FIGS. 6-8. In addition, the widths of the wipers in each set can be selected to meet the dimensions or shapes of particular sections of the coagulator. Preferably, the wipers 62, 64 are molded or formed as a single piece with the remainder of the tubular member 60 to reduce manufacturing costs and increase the structural integrity of the assembly.

The cleaner shown in FIGS. 6-8 has a generally cylindrical housing 10 with a generally cylindrical interior chamber. The tubular member 60 is also generally cylindrical in this embodiment. However, it should be understood that other cross-sectional shapes (e.g., elliptical, hexagon, octagonal, square or rectangular) could be employed.

The embodiment of the present invention shown in FIGS. 6-8 includes an end cap 70 that serves to hold the tubular member 60 in place within the cleaner housing 30, and also to guide the tip of a coagulator along the central axis of the cleaner, through the tubular member 60, and onto the prong 20. The embodiment of the end cap 70 depicted in FIG. 6 features a conically-tapered, annular insertion guide 72 that directs the tip of a coagulator toward a circular opening 74 on the central axis of the cleaner. The insertion guide 72 should have a diameter roughly corresponding to that of a conventional coagulator. Optionally, the insertion guide 72 can be made of a thin layer of material having a degree of elasticity, and the opening 74 can have a diameter slightly smaller than that of the coagulator. In this configuration, the perimeter of the insertion guide 72 surrounding the opening 74 stretches slightly to admit the coagulator and helps to clean the outer surface of the coagulator by wiping against it during insertion.

This type of end cap 70 offers several advantages, including ease of manufacture and assembly. However, it should be understood that the end cap 70 could be omitted. For example, the cleaner housing 10 could be fabricated in multiple pieces that contain the tubular member 60 when assembled. The device could also be assembled from the opposite end of the cleaning housing 10 containing the base 40 and prong 20.

The above disclosure sets forth a number of embodiments of the present invention described in detail with respect to the accompanying drawings. Those skilled in this art will appreciate that various changes, modifications, other structural arrangements, and other embodiments could be practiced under the teachings of the present invention without departing from the scope of this invention as set forth in the following claims.

I claim:

1. A device for cleaning a coagulator having a tube with a distal tip, said device comprising:
   a housing defining an interior chamber with sidewalls, a base, and a central axis extending through the base;
   a prong extending into the chamber from the base along the central axis to receive a coagulator bore;
   an insertion guide with an opening along the central axis guiding insertion of the tip of a coagulator onto the prong; and
   a tubular member made of a pliable material, insertable into the chamber with a central passageway aligned with the central axis, and including a plurality of pliable wipers extending radially inward into the central passageway toward the prong, whereby the wipers deform by contact to wipe against the coagulator.

2. The device of claim 1 wherein the insertion guide is conically tapered toward the opening.

3. A device for cleaning a coagulator comprising:
   a housing defining an internal chamber with sidewalls, a base, and a central axis extending through the base;
   a prong extending into the chamber from the base along the central axis to receive a coagulator bore;
   a tubular member made of a pliable material and insertable into the chamber, said tubular member having a central passageway aligned with the central axis of the chamber and a plurality of pliable wipers extending radially inward into the central passageway toward the prong, whereby the wipers deform by contact to wipe against the coagulator.

4. The device of claim 3 further comprising an insertion guide with an opening along the central axis of the chamber, said insertion guide guiding insertion of the tip of a coagulator through the central passageway of the tubular member and onto the prong.

5. The device of claim 4 wherein the insertion guide is conically tapered toward the opening.

6. The device of claim 3 wherein the sidewalls of the chamber are substantially cylindrical.

7. The device of claim 6 wherein the tubular member is substantially cylindrical and is held by contact with the sidewalls of the chamber.

8. The device of claim 3 further comprising an end cap containing the tubular member within the chamber and having an insertion guide with an opening along the central axis of the chamber, said insertion guide guiding insertion of the tip of a coagulator through the central passageway of the tubular member and onto the prong.

9. The device of claim 3 further comprising complementary alignment ribs and slots on the tubular member and sidewalls of the chamber allowing insertion of the tubular member into the chamber, but preventing rotation of the tubular member with respect to the housing.

10. The device of claim 3 wherein the tubular member and wipers are formed as a single piece.

11. The device of claim 3 wherein said pliable wipers comprise a plurality of sets of pliable wipers spaced axially along the tubular member.

12. The device of claim 11 wherein the sets of pliable wipers have differing dimensions selected to complement the shape of the coagulator.

\* \* \* \* \*